US00PP30042P3

(12) United States Plant Patent
Layt

(10) Patent No.: US PP30,042 P3
(45) Date of Patent: Jan. 1, 2019

(54) ***PANDOREA* PLANT NAMED 'PJ01'**

(50) Latin Name: *Pandorea jasminoides*
Varietal Denomination: PJ01

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 0 days.

(21) Appl. No.: 15/731,796

(22) Filed: Aug. 2, 2017

(65) Prior Publication Data

US 2018/0042156 P1 Feb. 8, 2018

(30) Foreign Application Priority Data

Aug. 2, 2016 (AU) ..... PBR 2016/213

(51) Int. Cl.
*A01H 5/02* (2018.01)
*A01H 5/04* (2018.01)

(52) U.S. Cl.
USPC ..... Plt./226
CPC ..... *A01H 5/02* (2013.01); *A01H 5/04* (2013.01)

(58) Field of Classification Search
USPC ..... Plt./226
CPC ..... A01H 5/02; A01H 5/04; A01H 6/00
See application file for complete search history.

*Primary Examiner* — June Hwu
(74) *Attorney, Agent, or Firm* — Samuel R. McCoy, Jr.

(57) ABSTRACT

A new and distinct *Pandorea* cultivar named 'PJ01' which is characterized by the combination of a compact and freely-branching growth habit, dense foliage, nearly pure white flowers, and the stability of these characteristics from generation to generation.

3 Drawing Sheets

Latin name of the genus and species: The Latin name of the genus and species of the novel variety disclosed herein is *Pandorea jasminoides*.

Variety denomination: The inventive cultivar of *Pandorea* disclosed herein has been given the variety denomination 'PJ01'.

CROSS REFERENCE TO RELATED APPLICATIONS

This application claims priority to the Australian Plant Breeders Rights application number 2016/213, filed on Aug. 2, 2016, which is herein incorporated by reference.

BACKGROUND OF THE INVENTION

Parentage: 'PJ01' is a seedling selection resulting from the open pollination of a small population of unnamed *Pandorea jasminoides* plants (not patented) at a commercial plant breeding facility in Clarendon, New South Wales, Australia in 2012. The inventor sowed seed collected from several of these unnamed *Pandorea jasminoides* plants and grew them to a mature size in order to evaluate for unique characteristics of commercial value. In October of 2013, the inventor observed that one seedling exhibited a smaller plant size with nearly pure white flowers. This seedling was isolated and further evaluated to assess the uniformity and stability of the characteristics first observed. After further evaluation, the claimed plant was selected for commercial production and given the name 'PJ01'.

Asexual Reproduction: Asexual reproduction of 'PJ01', by way of semi-hardwood stem cuttings, was first performed in May of 2014 in Cobbitty, New South Wales, Australia. Through five subsequent generations, the unique features of this cultivar have proven to be stable and true to type.

SUMMARY OF THE INVENTION

The cultivar 'PJ01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'PJ01'. These characteristics in combination distinguish 'PJ01' as a new and distinct *Pandorea jasminoides* cultivar:

1. *Pandorea* 'PJ01' exhibits a vining, freely branching growth habit with a relatively fast rate of growth; and
2. *Pandorea* 'PJ01' exhibits a relatively compact plant form with shortened internode length and dense foliage, from the base of the plant to the apex.
3. *Pandorea* 'PJ01' exhibits green, glossy foliage; and
4. *Pandorea* 'PJ01' exhibits nearly pure white flowers.

BOTANICAL DESCRIPTION OF THE PLANT

Figure 1:
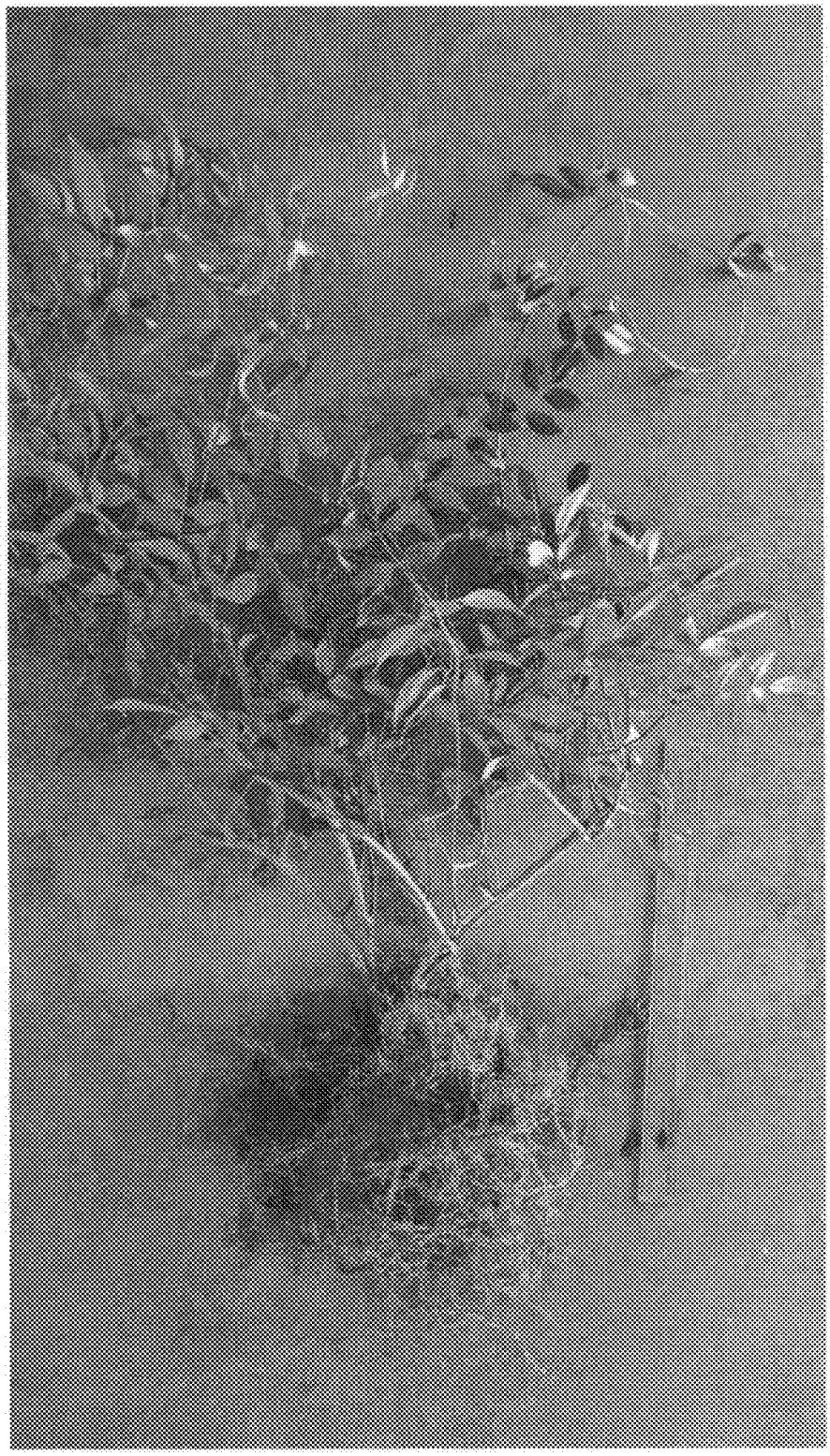
FIG. 1 illustrates, as nearly true as it is reasonably possible to make the same in color photographs of this type, an exemplary 3 year old 'PJ01', field-grown in Clarendon, New South Wales, Australia. The plant has been removed from the growing container and the soil removed to expose the roots.
Figure 2:
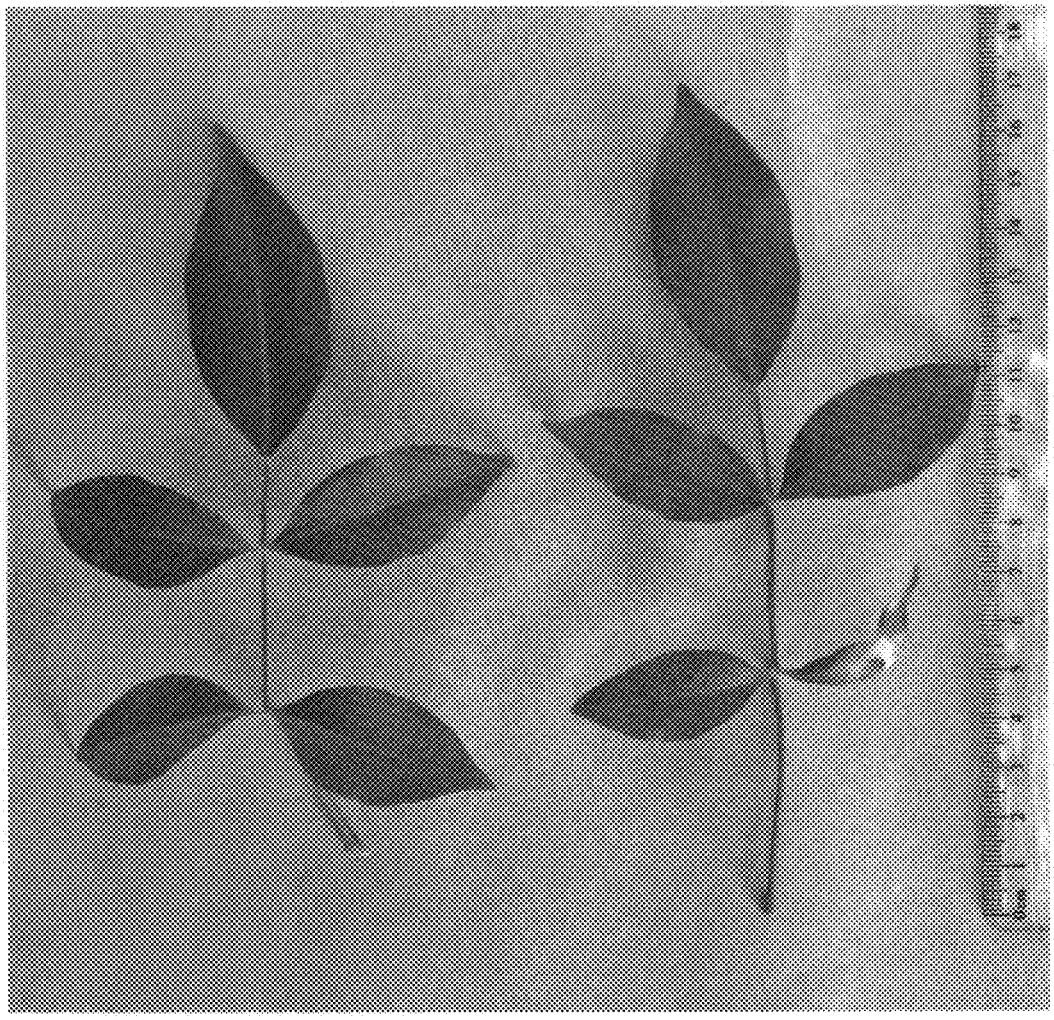
FIG. 2 illustrates, as nearly true as it is reasonably possible to make the same in color photographs of this type, the typical mature foliage of 'PJ01'.
Figure 3:
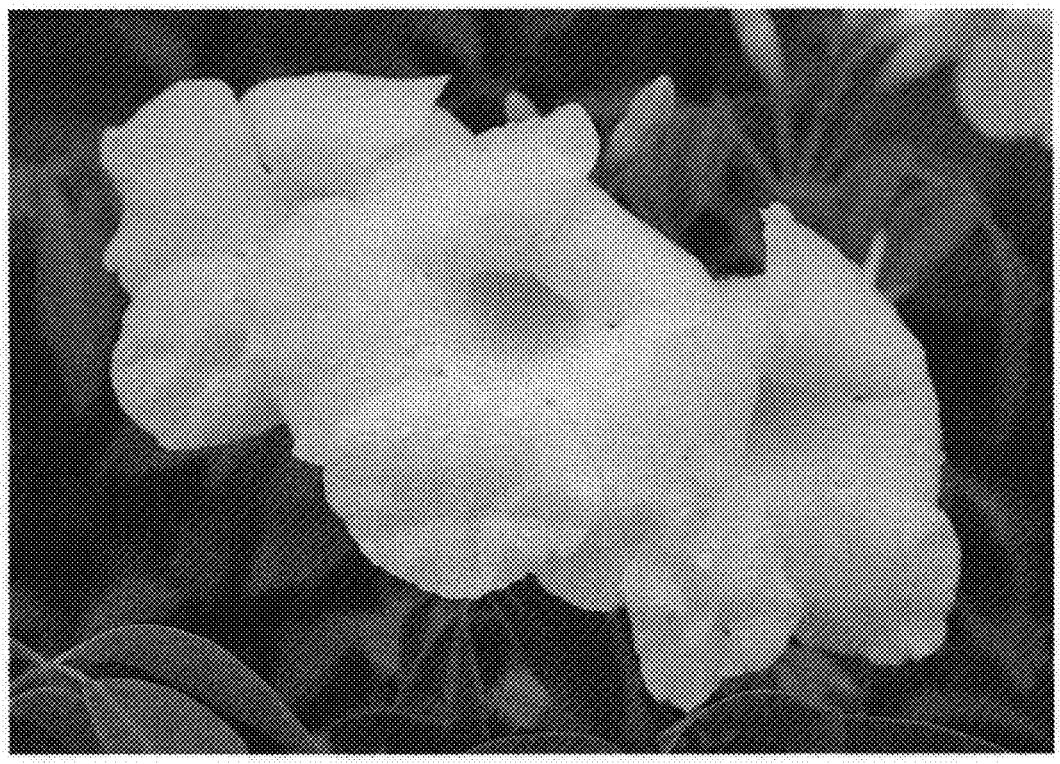
FIG. 3 illustrates, as nearly true as it is reasonably possible to make the same in color photographs of this type, the typical flower of 'PJ01'.

The following observations and measurements made in February of 2017 and, unless otherwise indicated, describe a 3 year old potted 'PJ01' field-grown plant produced in a 30 cm container in Clarendon, New South Wales, Australia. Plants were produced under shade, using conventional production protocols for *Pandorea* which consisted of regular overhead irrigation and controlled-release fertilizer applications. No chemical pest or disease measures were utilized in production.

Those skilled in the art will appreciate that certain characteristics will vary with older or, conversely, with younger plants. 'PJ01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition.

A botanical description of 'PJ01' and a comparison with the parent plant and the most similar commercial *Pandorea* cultivar known to the inventor, is provided below.

Plant description:

*Growth habit*.—Evergreen woody vine.

*Plant form*.—Compact; densely foliaged.

*Average height*.—80 cm, as observed.

*Average width*.—30 cm, as observed.

*Plant vigor*.—Vigorous.

*Propagation details*.—Asexual propagation may be accomplished by semi-hardwood stem cuttings with one to two nodes.

*Time to initiate roots*.—Approximately 4 to 6 weeks are required to initiate roots from a cutting.

*Time to produce a marketable rooted cutting*.—Approximately 16 weeks when propagated in the spring.

*Disease and pest resistance or susceptibility*.—Neither tolerance nor resistance to normal diseases and pests of *Pandorea* have been observed.

*Environmental tolerances*.—Hardy to USDA Hardiness Zone 9. Generally drought tolerant and tolerant of light frost once established.

Root system:

*General*.—Fibrous; freely branched and moderately dense rooting.

*Distribution in the soil profile*.—Moderately deep.

*Texture*.—Smooth.

*Color*.—Greyed-yellow, nearest to RHS 160D.

Stems:

*Branching habit*.—Multiple main stem, basally branching, and giving rise to numerous lateral branches.

*Main stems*.—Quantity — 4. Attitude — Semi-erect to erect. Cross-section — Rounded. Diameter — 1.2 cm at the base. Internode length — Ranging from 2.5 to 7.0 cm. Color — Greyed-brown, RHS 199B. Texture — Fissured. Strength — Strong.

*Lateral branches*.—Aspect — Vining; unsupported branches are prostrate to decumbent. Shape — Rounded. Strength — Weak to moderately strong. Diameter of lateral branches — Largest branches are 6.5 mm at the base. Internode length on lateral branches — 75 mm on average. Texture — Smooth; glabrous. Color — Yellow-green, nearest to RHS 144A.

Foliage:

*Arrangement*.—Opposite.

*Attachment*.—Petiolate.

*Division*.—Imparipinnate compound leaf, typically with 5 leaflets.

*Overall dimensions*.—16 cm long and 9.5 cm wide, on average.

*Foliage density on lateral branch*.—Very dense.

*Leaflets*.—Dimensions — Terminal leaflet is approximately 6.5 cm long and 2.9 cm wide; lateral leaflets are approximately 5.5 cm long and 2.2 cm wide. Shape — Ovate. Aspect — Involute. Apex — Acuminate. Base — Cuneate. Margin — Entire; slightly undulated. Texture and luster of adaxial surface — Smooth, glabrous and glossy. Texture and luster of abaxial surface — Smooth, glabrous and glossy. Color — Juvenile foliage, adaxial surface — Yellow-green, RHS 144A. Juvenile foliage, abaxial surface — Yellow-green, RHS 144B. Mature foliage, adaxial surface — Yellow-green, RHS 144A. Mature foliage, abaxial surface — Yellow-green, RHS 144B. Venation — Pattern — Pinnate. Color, adaxial surface — Yellow-green, RHS N144D. Color, abaxial surface — Yellow-green, RHS N144D.

*Petiole*.—Length — 48 mm. Width — 1.75 mm. Texture and luster — Glabrous, smooth, and moderately glossy. Strength — Weak. Color — Yellow-green, RHS N144D.

*Rachis*.—Length — 35 mm. Width — 1.5 mm. Texture and luster — Glabrous, smooth, and moderately glossy. Strength — Weak. Color — Yellow-green, RHS N144D.

Inflorescence:

*Type*.—Terminal panicle.

*Natural flowering season*.—Spring and autumn in New South Wales, Australia.

*Flowering habit*.—Freely flowering.

*Quantity of flowers per inflorescence*.—Typically 6.

*Attitude*.—Upward and outward.

*Peduncles*.—Length — 53 mm. Diameter — 4.0 mm at the base. Attitude — Upright. Strength — Medium. Texture — Smooth; glabrous. Luster — Matte to slightly glossy. Color — Yellow-green, nearest to RHS 144A.

Flower buds:

*Shape*.—Outline is oblong.

*Length*.—Average of 34 mm, prior to flowers opening.

*Diameter*.—Average of 14 mm, prior to flowers opening.

*Texture*.—Smooth; glabrous.

*Luster*.—Matte to slightly glossy.

*Color*.—Green-white, RHS 157C.

Flower:

*Shape*.—Salverform.

*Flower diameter*.—6.5 cm.

*Flower length*.—6.5 to 7.0 cm.

*Floral throat diameter*.—0.3 cm.

*Floral throat texture*.—Pubescent.

*Diameter of floral tube*.—2.0 cm at the distal end.

*Length of floral tube*.—3.5 cm.

*Floral tube texture*.—Pubescent.

*Aspect*.—Flowers are outward facing.

*Fragrance*.—Sweet fragrance.

*Lastingness*.—Approximately 5 days.

*Persistent*.—Self-cleaning.

*Pedicels*.—Dimensions — 12 mm long and 1.25 mm in diameter. Strength — Medium. Texture — Smooth; glabrous. Luster — Matte. Color — Yellow-green, nearest to RHS 144A.

*Petals*.—Quantity of Petals — 5. Arrangement — Single whorl; petals imbricate and fused into an elongated tube at the base; approximately 50 to 60 percent of the proximal portion of the petals are fused. Shape of petal lobes — Spatulate. Length, free portion of the petal — Ranging from 24 to 31 mm. Width, free portion of the petal — Ranging from 24 to 31 mm. Apex — Rounded. Base — Truncate; fused at the base. Margin — Cilliate; undulated. Aspect — Moderately reflexed. Texture and luster of upper surface — Velvety and matte. Texture and luster of lower surface — Velvety and matte. Petal lobe color when opening, upper surface — White, nearest to NN155C. Petal lobe color when opening, lower surface — White, nearest to NN155C. Petal lobe color when fully opened, upper surface — White, nearest to NN155C. Petal lobe color when fully opened, lower surface — White, nearest to NN155C. Petal venation — No venation is visible. Floral throat color — White, nearest to RHS NN155C. Floral throat venation color — No veins are visible. Inner corolla tube color, when fully opened — White, nearest to RHS NN155C, and lightly suffused with green-yellow, nearest to RHS 2D. Outer corolla tube color, when fully opened — White, nearest to NN155C. Floral tube venation color — No veins are visible.

*Calyx*.—Shape — Campanulate. Length — 10 mm. Diameter — 6.5 mm. Sepal lobes — Length — 2.0 mm. Width — 3.5 mm at the base of the sepal lobe. Arrangement — Campanulate. Quantity — 5. Shape — Deltoid. Apex — Acute. Base — Fused. Sepal lobe margin — Entire; not undulated. Pubescence, texture and luster — Smooth, glabrous, and matte. Color when fully opened — Yellow-green, nearest to RHS 144A, and fading to a mixture of white and green-yellow at the sepal lobes, RHS NN155C and 2D.

Reproductive organs:

*Androecium*.—Stamens — Quantity — 4. Anthers — Attachment — Dorsifixed. Shape — Two-lobed; lobes oblong. Dimensions — Approximately 5.5 mm long and 1.0 mm wide. Color — White, RHS NN155C. Filaments — Dimensions — 16 mm long and 0.5 mm in diameter. Color — White, nearest to RHS NN155D and slightly translucent. Pollen, amount — Moderately abundant. Pollen color — White, RHS NN155C.

*Gynoecium*.—Pistil — Quantity — 1. Style — Length — 15 mm. Color — White, nearest to RHS NN155D. Stigma — Shape — Globose. Length — 1.5 mm. Diameter — 1.5 mm. Color — White, nearest to RHS NN155D. Ovary Color — Yellow-green, nearest to in between RHS 144C.

Seed and fruit: Not observed.

COMPARISON WITH THE PARENT

Plants of the new cultivar 'PJ01' may be distinguished from its parent, an unnamed *Pandorea jasminoides* plant (not patented), by the characteristics described in Table 1.

TABLE 1

| Characteristic | 'PJ01' | The parent. |
|---|---|---|
| General coloration of the flower. | White. | Pink. |
| Internode length. | Medium. | Long. |

COMPARISON WITH THE CLOSEST KNOWN COMMERCIAL COMPARATOR

Plants of the new cultivar 'PJ01' may be distinguished from the most similar known commercial comparator, *Pandorea* 'Lady Di' (not patented), by the characteristics described in Table 2.

TABLE 2

| Characteristic | 'PJ01' | 'Saxon Gold' |
|---|---|---|
| Plant size. | Medium. | Large. |
| Internode length. | Medium. | Long. |

That which is claimed is:

1. A new and distinct cultivar of *Pandorea* plant named 'PJ01', substantially as described and illustrated herein.

* * * * *